United States Patent [19]

Bjornson

[11] 4,304,943

[45] Dec. 8, 1981

[54] CONVERSION OF ALKYL AND ARYL HYDROXY COMPOUNDS PRODUCING ALDEHYDE, ALCOHOL AND KETONE USING MANGANESE OXIDE/NICKEL OXIDE/MAGNESIUM OXIDE CATALYSTS

[75] Inventor: Geir Bjornson, Bartlesville, Okla.

[73] Assignee: Phillips Petroleum Company, Bartlesville, Okla.

[21] Appl. No.: 64,968

[22] Filed: Aug. 8, 1979

[51] Int. Cl.$^3$ .................... C07C 45/00; C07C 47/02; C07C 29/20

[52] U.S. Cl. ............................. 568/361; 568/403; 568/485; 568/832; 568/835

[58] Field of Search ............. 260/586 P, 596, 603 R; 568/832, 361, 403, 485, 835

[56] References Cited

U.S. PATENT DOCUMENTS

| | | | |
|---|---|---|---|
| 2,549,520 | 4/1951 | Prichard | 260/586 P |
| 3,305,586 | 2/1967 | Phielix | 260/586 P |
| 3,305,587 | 2/1967 | Sperbert et al. | 260/586 P |
| 3,420,887 | 1/1969 | Noddings et al. | 260/586 P |
| 3,422,146 | 1/1969 | Defoor et al. | 260/586 P |
| 3,446,850 | 5/1969 | Cotrupe et al. | 260/586 P |
| 3,689,544 | 9/1972 | Scanlon et al. | 260/429 J |
| 3,778,477 | 12/1973 | Mueller et al. | 260/586 P |
| 3,884,981 | 5/1975 | Kiff | 260/603 R |
| 3,941,845 | 3/1976 | Voskuil et al. | 260/586 R |
| 3,974,221 | 8/1976 | Duggan | 260/586 P |
| 3,998,884 | 12/1976 | Gibson | 260/586 P |
| 4,053,524 | 10/1977 | Stapp et al. | 260/586 P |
| 4,154,762 | 5/1979 | Huang et al. | 260/596 |

OTHER PUBLICATIONS

Kirk–Othmer Encyclopedia of Chemical Technology, 2nd Ed., vol. 6, pp. 684–686, John Wiley & Sons, (1965).

*Primary Examiner*—Natalie Trousof
*Assistant Examiner*—Vera C. Clarke

[57] ABSTRACT

Alkyl and aryl hydroxy compounds are converted to aldehydes, alcohols, and ketones in the presence of hydrogen using a catalyst comprised of the oxides of manganese, nickel and magnesium.

12 Claims, No Drawings

CONVERSION OF ALKYL AND ARYL HYDROXY COMPOUNDS PRODUCING ALDEHYDE, ALCOHOL AND KETONE USING MANGANESE OXIDE/NICKEL OXIDE/MAGNESIUM OXIDE CATALYSTS

BRIEF SUMMARY OF THE INVENTION

Alkyl and aryl hydroxy compounds are subjected to elevated temperature and hydrogen in the presence of a catalyst comprising manganese oxide/nickel oxide/magnesium oxide. Aliphatic alcohols are converted to aldehyde and ketone. Aromatic hydroxy compounds are converted to cycloaliphatic alcohol and ketone.

DETAILED DESCRIPTION

This invention relates to the conversion of alkyl and aryl hydroxy compounds. In one of its aspects, the invention relates to the conversion of an alkyl and/or an aryl hydroxy compound to at least one of an aldehyde, alcohol and ketone under dehydrogenation conditions. In another of its aspects, the invention relates to the production of useful compounds employing a catalyst essentially comprising manganese oxide, nickel oxide and magnesium oxide.

In one of its concepts the invention provides a method for converting an alkyl and/or an aryl hydroxy compound under dehydrogenation conditions to produce usable compounds, e.g., an aldehyde, alcohol, and/or ketone employing a catalyst essentially comprising manganese oxide, nickel oxide, and magnesium oxide. In another of its concepts, the invention provides a method for converting an aliphatic alcohol to an aliphatic aldehyde and/or ketone by subjecting the same to dehydrogenation conditions in the presence of a catalyst that is herein described. In another of its concepts, the invention provides a process for the conversion of an aromatic hydroxy compound to at least one of a cycloaliphatic alcohol and a cycloaliphatic ketone by subjecting the same in the presence of hydrogen to the action of a catalyst as herein described. In a more specific concept of the invention, it provides a method for preparing an aliphatic aldehyde from a primary aliphatic alcohol subjecting the same under dehydrogenation conditions to the action of a catalyst as herein described. Further, in another concept of the invention it provides a process for converting an aliphatic secondary alcohol to an aliphatic ketone by subjecting said alcohol to dehydrogenation conditions employing a catalyst as herein described. Still, in a further concept of the invention, it provides a method for preparing a cycloaliphatic alcohol from an aromatic hydroxy compound by subjecting the same to dehydrogenation conditions in the presence of a catalyst as herein described. Further, still, in another concept of the invention it provides a method of preparing a cycloaliphatic ketone from an aromatic hydroxy compound.

Aldehydes, alcohols and ketones have a wide range of applications that include solvents, additives and intermediates in the preparation of polymers such as nylon, dyes, surfactants, pharmaceuticals, and rubber chemicals. Some of the more widely known materials are methyl ethyl ketone, prepared by dehydrogenation or oxidation of 2-butanol; cyclohexanone, prepared by the dehydrogenation of cyclohexanol or air oxidation of cyclohexane; and cyclohexanol, prepared by the hydrogenation of aryl hydroxy compounds such as mixed cresols.

Methods are known for preparing the various products which are prepared herein employing the process of the present invention.

U.S. Pat. No. 3,884,981 discloses the use of the oxides of chromium, manganese and nickel in a hydrogenolysis-dehydrogenation of 2-butanol to methyl ethyl ketone. A two-component feed required is comprised of sec-butanol plus sec-butyl acetate. U.S. Pat. No. 3,420,887 describes the conversion of aliphatic alcohols to their corresponding aldehydes and ketones such as 2-butanol to methyl ethyl ketone and 1-butanol to 1-butanal using a calcium nickel phosphate catalyst. U.S. Pat. No. 3,998,884 employs metallic nickel on an inert support to convert phenol to cyclohexanol and cyclohexanone using controlled amounts of water.

It is of economic and chemical importance, particularly in times of reactant short supply, to have alternate methods of preparation or alternate catalyst systems that can be used to make the various types of aldehydes, alcohols and ketones.

It is an object of this invention to convert an alkyl and/or aryl hydroxy compound. It is another object of this invention to convert such compounds to at least one of an aldehyde, alcohol, and ketone. It is a still further object of the invention to provide an alternate process for the preparation of known compounds. Another object of the invention is to provide a catalytic process for the conversion of an alkyl and/or aryl hydroxy compound. A still further object of the invention is to provide a catalytic process for the conversion of at least one of an alkyl and an aryl hydroxy compound to at least one of an aldehyde, alcohol and ketone.

Other aspects, concepts, objects and the several advantages of the invention are apparent from a study of this disclosure and the appended claims.

According to the present invention there is provided a process for the conversion of at least one of an alkyl, an aryl hydroxy compound to a useful product which comprises subjecting at least one of said alkyl and aryl hydroxy compound to the action of hydrogen, under reaction conditions including a catalyst comprising the oxides of manganese, nickel, and magnesium.

The following feedstocks are presently contemplated and are included within the scope of the claimed invention.

ALIPHATIC PRIMARY ALCOHOLS

Materials useful in this invention to prepare aliphatic aldehydes are those aliphatic primary alcohols represented by the formula

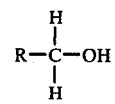  (I)

wherein R can be any alkyl or cycloalkyl radical having from 1 to 20 carbon atoms. For example, materials to be used that correspond to formula I can be, but not limited to ethanol
1-propanol
1-butanol
2-methyl-1-propanol
2-methyl-1-butanol 3-methyl-1-butanol
2,2-dimethyl-1-propanol
2-methyl-1-pentanol
1-hexanol
1-heptanol
1-dodecanol
and the like and mixtures thereof.

ALIPHATIC SECONDARY ALCOHOLS

Materials useful in this invention to prepare aliphatic ketones are those aliphatic secondary alcohols represented by the formula

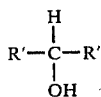 (II)

wherein each R' can be the same or different and can be any alkyl or cycloalkyl radical having from 1 to 10 carbon atoms. For example, materials to be used that correspond to formula II can be, but not limited to 2-propanol
2-butanol
2-pentanol
3-pentanol
3-methyl-2-butanol
2-hexanol
3-hexanol
2,2-dimethyl-3-butanol
2-decanol
3-decanol
2-dodecanol
3-dodecanol
and the like, and mixtures thereof.

AROMATIC HYDROXY COMPOUNDS

Materials useful in this invention to prepare cycloaliphatic alcohols and cycloaliphatic ketones are those aromatic hydroxy compounds represented by the formula

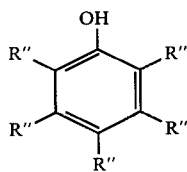 (III)

wherein R" can be hydrogen or any alkyl or cycloalkyl radical having from 1 to 6 carbon atoms. For example, materials to be used that correspond to formula III can be, but not limited to phenol
o-cresol
m-cresol
p-cresol
2,3-xylenol
2,4-xylenol
2,5-xylenol
2,6-xylenol
3,4-xylenol
3,5-xylenol
2,3,4-trimethylphenol
2,3,5-trimethylphenol
2,3,6-trimethylphenol
2,4,6-trimethylphenol
3,4,5-trimethylphenol
2-ethylphenol
2-hexylphenol
2,4-dihexylphenol
2-methyl-4-ethylphenol
2-cyclohexylphenol
and the like and mixtures thereof.

A small amount of water (e.g. 2 wt.%) can be present in the feed but it is not required nor does it appear now to be beneficial in any way. Water is sometimes present in such feeds because of insufficient drying. The invention accomodates well to such water.

The catalyst system of the current invention has been disclosed and claimed elsewhere.

The method of preparing the catalyst useful in this invention can be conventional and any known method can be used. The essential elements of the catalyst are manganese oxide, nickel oxide and magnesium oxide supplied by impregnation of the latter oxide with an aqueous solution of manganese nitrate and nickel nitrate. Alumina, which is known in the art as a nickel oxide activator or promoter can be present with the magnesium oxide. The nickel oxide/manganese oxide/magnesium oxide catalyst is somewhat brittle with little cohesive strength. The cohesive strength can be increased by use of a binder. Such a binder can be a blend of fumed silica (Cab-O-Sil$^R$) and water glass (sodium silicate plus water). The hydrated catalyst is dried, preferably under vacuum followed by calcining with air or nitrogen or mixtures thereof at 204° C. followed by a subsequent heating at 400° C. for 30 minutes in the presence of hydrogen. Hydrogen reduces the metal oxide to its lowest possible valence state while still an oxide. The hydrogen pre-treatment also helps to maintain catalyst composition consistency before the feed is introduced. The initial heating or activation of these nitrate type catalysts should be done outside the reactor because of the nitrous and nitric acid by-products formed during heating that can be harmful to the metal reactor or metal packing. Thereafter, the catalyst can be regenerated in the tubular reactor by passing nitrogen, air, or mixtures thereof over the catalyst at about 200° C. to 400° C.

The amount of manganese oxide present expressed as free manganese can be broadly 5 to 30 wt. precent of the total catalyst system but it is preferred to be about 10 to 25 wt. percent.

The amount of nickel oxide present expressed as free nickel can be broadly 2 to 25 wt. percent of the total catalyst system but it is preferred to be about 5 to 20 wt. percent. The ratios of nickel oxide to manganese oxide again expressed as the free metal can be

|  | Broadly | Preferred |
| --- | --- | --- |
| nickel/manganese, molar ratio | 0.1/1–3/1 | 0.2/1–2/1 |
| nickel/manganese, wt. ratio | 0.1/1–3/1 | 0.2/1–2/1 |

The magnesium oxide employed can be as a pellet to which the aqueous nitrate solutions are mixed and heated or in the form of a water soluble hydroxide which is subsequently decomposed to magnesium oxide. If pelleted or granulated magnesium oxide is employed it is preferred that the particle size be less than 50 mesh as measured by a U.S. Standard sieve screen although any convenient size can be used. The amount of magnesium oxide present expressed as free metal can be broadly 50 to 90 wt. percent of the total catalyst system but it is preferred to be about 60 to 80 wt. percent.

The amount of hydrogen used is expressed as the mole ratio of hydrogen to reactant feed (undiluted) and can be broadly from 1:1 to 20:1 but preferably from 1:1 to about 10:1. Hydrogen can be diluted with inert gases such as nitrogen.

The use of solvents in this invention is optional. The amount of solvent used can be about 25 to 75 wt. percent of the total feed. Solvents useful are the alkanes and cycloalkanes having from about 5 to 7 carbon atoms such as pentane, hexane, heptane, methylcyclopentane, cyclohexane, and the like.

| E. Reaction Conditions | Broad | Preferred |
|---|---|---|
| 1. Temperatures | | |
| °F. | 400–900 | 600–800 |
| °C. | 204–482 | 315–426 |
| 2. Pressures | | |
| psi | 50–600 | 75–500 |
| MPa | 0.344–4.138 | 0.517–3.448 |
| 3. Flow Rates | | |
| Liquid Hourly Space Velocity (LHSV) | 0.1–10 | 0.5–5.0 |

The following examples serve to illustrate the operability of this invention.

EXAMPLE I

This example illustrates the usefulness of the inventive catalyst, MnO/NiO/MgO, in the conversion of a secondary alcohol, 2-butanol, to a ketone, methyl ethyl ketone (MEK). The catalyst was prepared as follows: To 30 milliliters of a 50 wt. % aqueous solution (from Mallinckrodt) which contained 23.4 grams of $Mn(NO_3)_2$ was added 30 milliliters of water and 9.5 grams of $Ni(NO_3)_2.6H_2O$. The resulting paste was slowly added to a vigorously stirred solution of 40.9 grams of MgO and 60 milliliters of water. The newly formed thick pasty-like mixture was poured into a 15.24 cm. (6 in.)×0.32 cm. (0.125 in.)×0.32 cm. (0.125 in.) rubber mold. At this point, the molar amounts of free metal available was estimated to be 1.01 moles of Mg; 0.13 moles of Mn; 0.033 moles of Ni. The ratio of active metals is shown below. Since the exact oxide form of the metal is not known, the values are expressed on the basis of free metal.

| Metal Ingredients | Proportions of Metals | | |
|---|---|---|---|
| | Molar Ratio[a] | Wt. Ratio %[a] | Wt. % |
| Manganese | 1.0 | 1.0 | 21.2 |
| Nickel | 0.25 | 0.27 | 5.7 |
| Magnesium | 7.77 | 3.44 | 73.1 |

[a]Based on 1.0 for manganese

After drying overnight at ambient room temperature, the mold and catalyst were placed in a vacuum oven (20 mm) at 93° C. (200° F.) for 2 hours. The slab of catalyst formed was broken into small pieces and calcined in a quartz tube with a 50:50 volume percent air and nitrogen, first at 316° C.–371° C. (600° F.–700° F.) to remove oxides of nitrogen, then at 482° C. (900° F.–950° F.). An alternate method of removing water and nitrogen oxides is to put the catalyst in a vacuum oven (<10 mm pressure) for 16-24 hours at 204° C. (400° F.). Catalyst dried by either method is activated by heating to about 10° C. (50° F.) above the desired operating temperature while a stream of hydrogen, containing some nitrogen initially, is passed through the reactor. The mole ratio of active nickel to manganese is estimated to be 0.25/1.0.

To a 316 stainless steel tubular reactor having the dimensions 2.44 cm. (0.960 in.) diameter by 70.49 cm. (27.75 in.) and equipped with an external electrical heater and a Moore back-pressure regulator was charged 60 milliliters of the catalyst described above mixed with about 73 milliliters of 316 stainless steel Helipak (0.125 in.×0.125 in.) which was used as a heat transfer agent to help control the temperature of the reaction which was usually exothermic. While the temperature was maintained at about 427° C. (900° F.) and 0.55 MPa (80 psi) $H_2$ pressure, 2-butanol was fed through the reactor at a rate of 40 milliliters per hour (0.665 LHSV), the pressure being maintained by hydrogen which mixes with the feed at a molar ratio of about 1.0 mole of hydrogen to 1.0 mole of 2-butanol. The effluent product was analyzed without further separation with a Bendix[R] 2300 chromatograph employing a column packed with Porapak (QS) from Waters Inc. This type column separates 2-butanol and MEK. The column was programmed as follows: 100° C. to 190° C. at 30° C./min.; 190° C. to 250° C. at 10° C./min.; and isothermal at 250° C. until complete. The analysis showed the following products: 0.77 wt. % 1-butene; 2.50 wt. % 2-butenes (c & t); 77.28 wt. % MEK; 13.97 wt. % 2-butanol; and 5.48 wt. % heavies. On the basis of the analysis, there was an 86.1% conversion of 2-butanol with a 89.8% selectivity to MEK. This run was repeated at several different temperatures. These results which are listed below indicate the highest MEK selectivities at about 343° C. (650° F.) but the highest 2-butanol conversion at 427° C. (800° F.).

TABLE I

Conversion of 2-Butanol to Methyl Ethyl Ketone (MEK)
Using the Catalyst MgO/MnO/NiO and 0.5 MPa (80 psi) Hydrogen Pressure

| Reaction Temp. | | % 2-Butanol Conversion | % Area by GLC | | | | | % MEK Selectivity[a] |
|---|---|---|---|---|---|---|---|---|
| °C. | °F. | | 2-Butanol | 1-Butene | 2-Butenes | MEK | Heavies | |
| 315 | 600 | 23.2 | 76.80 | 0.29 | 0.73 | 20.74 | 1.44 | 89.4 |
| 332 | 630 | 21.4 | 78.56 | 0.19 | 0.53 | 20.57 | 0.15 | 95.9 |
| 343 | 650 | 24.3 | 75.72 | 0.18 | 0.56 | 23.44 | 0.10 | 96.5 |
| 371 | 700[b] | 43.9 | 56.16 | 0.30 | 0.81 | 40.62 | 2.13 | 92.9 |
| 398 | 750 | 62.0 | 38.04 | 0.49 | 0.87 | 57.13 | 3.47 | 92.2 |
| 427 | 800 | 86.1 | 13.97 | 0.77 | 2.50 | 77.28 | 5.48 | 89.8 |

[a]% Area MEK ÷ Total % Areas = % MEK Selectivity. 2-Butanol considered recyclable.
[b]Values result of 2 runs.

EXAMPLE II

This example illustrates the use of a control catalyst, MnO/MgO, *without* NiO. To 29.6 milliliters of a 50 wt. % aqueous solution which contained 23.1 grams (0.13 moles) of Mn(NO$_3$)$_2$ was added 59.1 grams (1.46 moles) of MgO (SMR-7-4938 from Grace Chemical Co.) along with 100 milliliters of water. The thick mixture was subsequently processed in the same manner as described in Example I.

The reactor experiment described in Example I was repeated using the catalyst MnO/MgO. These results are listed in Table II and show lower selectivities to MEK than those obtained at comparable temperatures with the inventive catalyst system containing NiO (see Table I).

TABLE II

Conversion of 2-Butanol to Methyl Ethyl Ketone (MEK) Using the Catalyst MnO/MgO and 0.5 MPa (80 psi) Hydrogen Pressure

| Reaction Temp. | | % 2-Butanol Conversion | % Area by GLC | | | | | | | % MEK Selectivity |
|---|---|---|---|---|---|---|---|---|---|---|
| °C. | °F. | | 2-Butanol | 1-Butene | 2-Butenes | MEK | Aldol 1[a] | Aldol 2[b] | Heavies | |
| 315 | 600 | 41.7 | 58.32 | 0.15 | 1.03 | 30.33 | 3.06 | 5.51 | 1.60 | 72.8 |
| 371 | 700 | 82.6 | 17.37 | 0.68 | 2.04 | 63.71 | 5.69 | 4.59 | 5.90 | 77.1 |

[a]1-Ethyl-3-methyl-pentenone
[b]1,2,3-Trimethyl-2-pentenone

EXAMPLE III

This example illustrates the usefulness of the inventive catalyst, MnO/NiO/MgO, in the conversion of a primary alcohol, 2-methyl-1-butanol, to an aldehyde, 2-methyl-1-butanol.

The reactor experiment described in Example I was repeated using the same catalyst, 1.01 moles Mg/0.13 moles Mn/0.033 moles Ni except the feed was 2-methyl-1-butanol. The hydrogen pressure was also the same. At 315° C. (600° F.), conversion was 34.2% with a 59.4% selectivity to 2-methyl-1-butanal. At 427° C. (800° F.), the conversion was 55.3% with an aldehyde selectivity of 92.3%.

In a second series of runs the amount of Ni(NO$_3$)$_2$.6 H$_2$O used in the catalyst system was increased from 9.50 grams to 14.25 grams. This changed the Ni/Mn mole ratio from 0.25/1 to 0.35/1. The increased nickel content lowered both the % conversion of 2-methyl-1-butanol and the % selectivity to the corresponding aldehyde. These results are shown in Table III.

TABLE III

Conversion of 2-Methyl-1-Butanol to 2-Methyl-1-Butanal Using the Catalyst MnO/NiO/MgO and 0.5 MPa (80 psi) Hydrogen Pressure

| Molar Ratio of Ni/Mn | Reaction Temp. | | % Conversion of 2-Methyl-1-Butanol | 2-Methyl-1-&2-Butenes | 2-Methyl-1-Butanal |
|---|---|---|---|---|---|
| | °C. | °F. | | | |
| ¼ | 315 | 600 | 34.2 | 0.2 | 59.4 |
| ¼ | 427 | 800 | 55.3 | 0.2 | 92.3 |
| ⅜ | 315 | 600 | 22.3 | 0.6 | 78.3 |
| ⅜ | 371 | 700 | 43.3 | 0.7 | 89.8 |
| ⅜ | 427 | 800 | 49.0 | 1.6 | 81.3 |

EXAMPLE IV

This example illustrates the use of a control catalyst, MnO/MgO, without NiO. The procedure described in Example II was repeated except the feed was 2-methyl-1-butanol instead of 2-butanol. These results are listed in Table IV and show much lower 2-methyl-1-butanol conversions than those obtained at comparable temperatures with the inventive catalyst system containing NiO (see Table III).

TABLE IV

Conversion of 2-Methyl-1-Butanol to 2-Methyl-1-Butanol Using the Catalyst MnO/MgO and 0.5 MPa (80 psi) Hydrogen Pressure

| Reaction Temp. | | % Conversion of 2-Methyl-1-Butanol | % Selectivity by GLC | |
|---|---|---|---|---|
| °C. | °F. | | 2-Methyl-1&2-Butenes | 2-Methyl-1-Butanol |
| 315 | 600 | 2.9 | 0.0 | 95.0 |
| 371 | 700 | 15.8 | 3.6 | 94.8 |
| 427 | 800 | 39.0 | 5.7 | 83.6 |

EXAMPLE V

This example illustrates the use of another control wherein the NiO portion of the inventive catalyst system was replaced with CaO. The catalyst was prepared in a similar manner as described herein using 90 grams (2.23 moles) MgO, 12.6 grams (0.053 moles) of Ca(NO$_3$)$_2$.4 H$_2$O, and 87 grams (0.24 moles) of a 50 wt. percent aqueous solution of Mn(NO$_3$)$_2$. The molar ratios of free metal was estimated at 1.0 moles Mg/0.11 moles Mn/0.023 moles Ca. The molar ratio of Ca to Mn was also estimated to be 1/4.5. The reactor runs described in Example I were repeated except the feed was 2-methyl-1-butanol and the catalyst was MgO/MnO/CaO. These results which are listed in Table V show very low 2-methyl-1-butanol conversions as compared to those obtained with the inventive catalyst at comparable temperatures (see Table IV).

TABLE V

Conversion of 2-Methyl-1-Butanol to 2-Methyl-1-Butanal Using the Catalyst MnO/MgO/CaO and 0.5 MPa (80 psi) Hydrogen Pressure

| Reaction Temp. | | % Conversion of 2-methyl-1-Butanol | % Selectivity by GLC | |
|---|---|---|---|---|
| °C. | °F. | | 2-Methyl-1&2-Butenes | 2-Methyl-1-Butanal |
| 315 | 600 | 1.6 | 0.0 | 91.6 |
| 371 | 700 | 4.1 | 3.5 | 94.1 |
| 427 | 800 | 13.1 | 4.5 | 91.3 |

EXAMPLE VI

This example illustrates the use of another control wherein the catalyst employed, cobalt molybdate on alumina, is also known as an olefin disproportionation catalyst and a hydrodesulfurization catalyst. The procedure described in Example III was repeated except the MnO/MgO/NiO was replaced with a cobalt molybdate on alumina catalyst (F-475-16, Filtrol Corp.). The results shown in Table VI show very high 2-methyl-1-butanol conversions but no 2-methyl-1-butanal product.

TABLE VI

Conversion of 2-Methyl-1-Butanol to 2-Methyl-1-Butanal Using the Catalyst Cobalt Molybdate on Alumina and 0.5 MPa (80 psi) Hydrogen Pressure

| Reaction Temp. °C. | °F. | % Conversion of 2-Methyl-1-Butanol | % Selectivity by GLC | | | |
|---|---|---|---|---|---|---|
| | | | 2-Methyl Butene-1 | 2-Methyl Butene-2's | 2-Methyl 1-Butanal | Others |
| 315 | 600 | 93.4 | 29.99 | 66.05 | 0 | 3.96 |
| 371 | 700 | 98.3 | 28.60 | 65.04 | 0 | 6.36 |

EXAMPLE VII

This is a control run using $Ca_3(PO_4)_2$ as a catalyst to replace the inventive catalyst MnO/NiO/MgO used in Example III. $Ca_3(PO_4)_3$ (N.F. powder from Mallinckrodt) was ground between steel rollers to a granular material of less than 8 mesh size before using. These results listed in Table VII show high aldehyde selectivity at 315° C. but low % conversion. As the temperature was increased, the % butanol conversion was increased but the aldehyde selectivity decreased.

TABLE VII

Conversion of 2-Methyl-1-Butanol to 2-Methyl-1-Butanal Using the Catalyst $Ca_3(PO_4)_2$ and 0.5 MPa (80 psi) Hydrogen Pressure

| Reaction Temp. °C. | °F. | % Conversion of 2-Methyl-1-Butanol | % Selectivity by GLC | | | |
|---|---|---|---|---|---|---|
| | | | 2-Methyl Butene-1 | 2-Methyl Butene-2's | 2-Methyl-1-Butanal | Others |
| 315 | 600 | 8.9 | 12.1 | 3.5 | 83.5 | 0.9 |
| 371 | 700 | 27.6 | 23.4 | 13.3 | 61.1 | 2.2 |
| 398 | 750 | 66.7 | 22.0 | 28.6 | 46.5 | 2.9 |

EXAMPLE VIII

This example illustrates the usefulness of the inventive catalyst, MnO/NiO/MgO, in converting aromatic hydroxy compounds into saturated ring alcohols and ketones. The inventive catalyst was basically the same as described in Example I except the molar ratio of Ni/Mn was changed from 0.25/1.0 to 1.7/1. In addition, a little fumed silica and sodium silicate (water glass) was added as a binder. The catalyst was prepared in the same manner as the inventive catalyst in Example I except from a solution containing 1.8 grams (0.004 moles) $Al(NO_3)_3.9\ H_2O$, 33.0 grams (0.113 moles) $Ni(NO_3)_2.6\ H_2O$, 11.7 grams (0.065 moles) $Mn(NO_3)_2$, 60 grams water, 59.1 grams (1.01 moles) $Mg(OH)_2$, 0.5 grams (0.008 moles) fumed $SiO_2$ (Cab-O-Sil[R]), and 6 milliliters of water glass (2 grams (0.007 moles) $Na_2SiO_3.9\ H_2O$). The ratio of active metals is shown below. Since the exact oxide form of the metal is not known, the values are expressed on the basis of free metal.

| Metal Ingredients | Proportions of Metals | | |
|---|---|---|---|
| | Molar Ratio[a] | Wt. Ratio[a] | Wt. % |
| Manganese | 1.0 | 1.0 | 10.2 |
| Nickel | 1.7 | 1.86 | 18.8 |
| Magnesium | 15.5 | 6.86 | 69.7 |
| Aluminum | 0.06 | 0.03 | 0.3 |

[a]Based on 1.0 for manganese.

The reactor run procedure described in Example I was repeated using the above catalyst and liquid o-cresol as the feed. The data listed in Table VIII shows about equal distribution in selectivity between 2-methylcyclohexanol and 2-methylcyclohexanone. Increasing hydrogen pressure favors the formation of 2-methylcyclohexanone.

TABLE VIII

Conversion of o-Cresol to 2-Methylcyclohexanol and 2-Methylcyclohexanone Using the Catalyst MnO/NiO/MgO at Various Hydrogen Pressures (Temp. 315° C., 600° F.)

| Reaction Pressure Mpa | psi | % Conversion | % Selectivity Based on GLC | | | | | | | |
|---|---|---|---|---|---|---|---|---|---|---|
| | | | Benzene | Toluene | Methyl-Cyclohexane | Xylenols | Cyclo-hexanol | Phenol | 2-Methyl-Cyclohexanone | 2-Methyl-Cyclohexanol[a] |
| 0.689 | 100 | 41.0 | 1.1 | — | — | 15.3 | 5.5 | 13.1 | 35.9 | 29.1 |
| 1.379 | 200 | 76.5 | 0.8 | 0.4 | 1.0 | 5.5 | 7.1 | 2.5 | 38.1 | 43.6 |
| 2.069 | 300 | 55.1 | 0.6 | 0.6 | 1.0 | 5.1 | 4.5 | 3.7 | 42.5 | 41.2 |

EXAMPLE IX

This example illustrates the usefulness of the inventive catalyst in Example VIII wherein the molar ratio of Ni/Mn is 1.7/1 and the feed was hot liquid m-cresol. In addition, another catalyst was used based on the inventive catalyst combination of MnO/NiO/MgO but where the molar ratio was changed to 0.25/1.0 of Ni/Mn. The data listed in Table IX shows good selectivity of the cis and trans 3-methylcyclohexanol although % m-cresol conversions are low. Increased hydrogen pressure favors the formation of 3-methylcyclohexanone. When the Ni/Mn is changed from 1.7/1 to 0.25/1 there still is some activity but the % m-cresol conversion is lowered.

TABLE IX

Conversion of m-Cresol (Temp. 315° C., 600° F.)

| Molar Ratio of Ni/Mn | Reaction Pressure MPa | psi | % Conversion | % Selectivity Based on GLC | | | | |
|---|---|---|---|---|---|---|---|---|
| | | | | Cyclo-Hexane | Toluene | Phenol | 3-Methyl-Cyclohexanone | 3-Methyl-Cyclohexanol[a] |
| 4/1 | 0.689 | 100 | 1.6 | — | 25.4 | — | — | 74.6 |
| 4/1 | 2.758 | 400 | 26.6 | 1.2 | 4.0 | 1.2 | 24.5 | 68.5 |
| ¼ | 0.689 | 100 | trace | — | — | — | — | — |
| ¼ | 2.758 | 400 | 15.1 | — | 2.1 | — | 34.9 | 65.1 |

[a]Includes cis and trans isomers

EXAMPLE X

This example illustrates the use of the inventive composition catalyst, MnO/NiO/MgO, wherein the molar ratio of Ni/Mn was 0.25/1.0 and the feed was hot liquid p-cresol. The results shown in Table X indicate low p-cresol conversion (25.9%) with the major product being 4-methylcyclohexanol.

Mn, as their oxides can function in molar ratios expressed as free metals varying from 0.25/1 to 1.7/1. With paraffinic alcohols the 0.25/1 Ni/Mn molar ratio works well but with aromatic hydroxy compounds a 1.7/1 Ni/Mn molar ratio works best.

It is evident from the foregoing that the process of the invention provides alternate and improved operation when considered in light of the prior art.

TABLE XI

Summary of MnO/NiO/MgO Catalyzed Reactions on Paraffinic and Aromatic Hydroxy Compounds

| Example | Catalyst | Approx. Molar Ratio Ni/Mn | Reaction Temp., °C. | Feed | % Feed Conversion | Principal Product(s) | % Product Selectivity |
|---|---|---|---|---|---|---|---|
| I | MnO/NiO/MgO | 0.25/1 | 371 | 2-Butanol | 43.9 | Methyl Ethyl Ketone | 92.9 |
| I | MnO/NiO/MgO | .25/1 | 427 | 2-Butanol | 86.1 | Methyl Ethyl Ketone | 89.8 |
| II | MnO/MgO | .25/1 | 371 | 2-Butanol | 41.7 | Methyl Ethyl Ketone | 72.8 |
| II | MnO/MgO | .25/1 | 427 | 2-Butanol | 82.6 | Methyl Ethyl Ketone | 77.1 |
| III | MnO/NiO/MgO | .25/1 | 427 | 2-Methyl-1-butanol | 55.3 | 2-Methyl-1-butanal | 92.3 |
| III | MnO/NiO/MgO | .35/1 | 371 | 2-Methyl-1-butanol | 43.3 | 2-Methyl-1-butanal | 89.8 |
| III | MnO/NiO/MgO | .35/1 | 427 | 2-Methyl-1-butanol | 49.0 | 2-Methyl-1-butanal | 81.3 |
| IV | MnO/MgO | — | 371 | 2-Methyl-1-butanol | 15.8 | 2-Methyl-1-butanal | 94.8 |
| IV | MnO/MgO | — | 427 | 2-Methyl-1-butanol | 39.0 | 2-Methyl-1-butanal | 83.6 |
| V | MnO/CaO/MgO | — | 371 | 2-Methyl-1-butanol | 4.1 | 2-Methyl-1-butanal | 94.1 |
| V | MnO/CaO/MgO | — | 427 | 2-Methyl-1-butanol | 13.1 | 2-Methyl-1-butanal | 91.3 |
| VI | Cobalt Molybdate/Al$_2$O$_3$ | — | 371 | 2-Methyl-1-butanol | 98.3 | 2-Methyl-1-butanal | 0 |
| VII | Ca$_3$(PO$_4$)$_3$ | — | 371 | 2-Methyl-1-butanol | 27.6 | 2-Methyl-1-butanal | 61.1 |

| Example | Catalyst | Approx. Molar Ratio Ni/Mn | Temp., °C. | H$_2$ Press. | Feed | % Feed Conversion | Principal Product(s) | % Product Selectivity |
|---|---|---|---|---|---|---|---|---|
| VIII | MnO/NiO/MgO[a] | 1.7/1 | 375 | 100 psi | o-cresol | 41.0 | 2-Methylcyclohexanone / 2-Methylcyclohexanol | 29.1 / 35.9 |
| VIII | MnO/NiO/MgO[a] | 1.7/1 | 315 | 200 psi | o-cresol | 76.5 | 2-Methylcyclohexanone / 2-Methylcyclohexanol | 38.1 / 43.6 |
| VIII | MnO/NiO/MgO[a] | 1.7/1 | 315 | 300 psi | o-cresol | 55.1 | 2-Methylcyclohexanone / 2-Methylcyclohexanol | 42.5 / 41.2 |
| IX | MnO/NiO/MgO | 1.7/1 | 315 | 100 psi | m-cresol | 0 | | |
| IX | MnO/NiO/MgO | 1.7/1 | 315 | 400 psi | m-cresol | 15.1 | 3-Methylcyclohexanone / 3-Methylcyclohexanol | 34.9 / 65.1 |
| IX | MnO/NiO/MgO | .25/1 | 315 | 100 psi | m-cresol | 1.6 | 3-Methylcyclohexanone / 3-Methylcyclohexanol | 0 / 74.6 |
| IX | MnO/NiO/MgO | 4/1 | 315 | 400 psi | m-cresol | 26.6 | 3-Methylcyclohexanone / 3-Methylcyclohexanol | 24.5 / 68.5 |
| X | MnO/NiO/MgO | 1/4 | 315 | 100 psi | p-cresol | 0 | 4-Methylcyclohexanone | 74.4 |
| X | MnO/NiO/MgO | 1/4 | 315 | 400 psi | p-cresol | 25.9 | 4-Methylcyclohexanol | 22.1 |

[a] Also contains <1 wt. % alumina and a binder based on fumed silica and sodium silicate (water glass).

TABLE X

Conversion of p-Cresol (Temp. 315° C., 600° F.)

| Reaction Pressure | | % Conversion | 4-Methyl-Cyclohexanone | 4-Methyl-Cyclohexanol[a] |
|---|---|---|---|---|
| MPa | psi | | | |
| 0.689 | 100 | trace | — | — |
| 2.758 | 400 | 25.9 | 74.4 | 22.1 |

[a] Includes cis and trans isomers.

The data herein disclosed is summarized in Table XI wherein it is seen the advantage of using the catalyst system MnO/NiO/MgO in the presence of hydrogen to convert secondary paraffinic alcohols to ketones, primary paraffinic alcohols to aldehydes and aromatic hydroxy compounds to cycloaliphatic alcohols and ketones. The metals considered most essential, Ni and Reasonable variation and modification are possible within the scope of the foregoing disclosure and the appended claims to the invention the essence of which is that at least one of an alkyl and an aryl hydroxyl compound is converted under dehydrogenation conditions in the presence of hydrogen and a catalyst comprised of the oxides of manganese, nickel and magnesium as herein described; and at good selectivities to desirable products are obtainable, also as herein described.

I claim:

1. A process for the dehydrogenation of at least one compound selected from the group consisting of alkyl and cycloalkyl hydroxy compounds, on the hydrogenation of an aryl hydroxy compound, which comprises subjecting said compound to the action of hydrogen under dehydrogenation conditions or hydrogenation conditions, respectively, in the presence of a catalyst comprising the oxides of manganese, nickel and magnesium, wherein the amounts of the oxides, expressed as free metals present, are 5-30, wt. % manganese, 2-25 wt. % nickel, and 50-90 wt. % magnesium.

2. A process according to claim 1 wherein the alkyl or cycloalkyl hydroxy compound is at least one of a primary alcohol and a secondary alcohol, the primary alcohol is represented by the formula

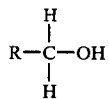

wherein R is selected from alkyl and cycloalkyl radicals having 1 to 20 carbon atoms, the secondary alcohol is represented by the formula

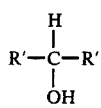

wherein each R' is selected from alkyl and cycloalkyl radicals having from 1 to 10 carbon atoms, and wherein the aryl hydroxy compound is represented by the formula

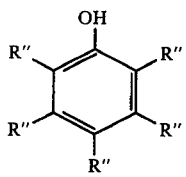

wherein each R'' is selected from hydrogen, alkyl and cycloalkyl radicals having from 1 to 6 carbon atoms.

3. A process according to claim 2 wherein the primary alcohol is at least one selected from the group consisting of
ethanol
1-propanol
1-butanol
2-methyl-1-propanol
2-methyl-1-butanol
3-methyl-1-butanol
2,2-dimethyl-1-propanol
2-methyl-1-pentanol
1-hexanol
1-heptanol and
1-dodecanol,
wherein the secondary alcohol is at least one selected from the group consisting of
2-propanol
2-butanol
2-pentanol
3-pentanol
3-methyl-2-butanol
2-hexanol
3-hexanol
2,2-dimethyl-3-butanol
2-decanol
3-decanol
2-dodecanol and
3-dodecanol,
and wherein the aryl hydroxy compounds is at least one selected from the group consisting of
phenol
o-cresol
m-cresol
p-cresol
2,3-xylenol
2,4-xylenol
2,5-xylenol
2,6-xylenol
3,4-xylenol
3,5-xylenol
2,3,4-trimethylphenol
2,3,5-trimethylphenol
2,3,6-trimethylphenol
2,4,6-trimethylphenol
3,4,5-trimethylphenol
2-ethylphenol
2-hexylphenol
2,4-dihexylphenol
2-methyl-4-ethylphenol and
2-cyclohexylphenol.

4. A process according to claim 1 wherein the respective weights percent are as follows: 10-25; 5-20; and 60-80.

5. A process according to claim 2 wherein 2-methyl-1-butanol is selected as the alkyl hydroxy compound and it is converted to 2-methyl-1-butanal.

6. A process according to claim 2 wherein the alkyl hydroxy compound selected is 2-butanol and it is converted to methyl ethyl ketone.

7. A process according to claim 2 wherein orthocresol is the aryl hydroxy compound selected and it is converted to 2-methylcyclohexanol and 2-methylcyclohexanone.

8. A process according to claim 2 wherein the aryl hydroxy compound selected is m-cresol and it is converted to cis- and trans-methylcyclohexanol.

9. A process according to claim 2 wherein the aryl hydroxy compound selected is p-cresol and it is converted to 4-methylcyclohexanol.

10. A process according to claim 1 wherein the molar ratio of nickel to manganese, expressed as the free metal, is in the range 0.1/1-3/1.

11. A process according to claim 1 wherein the nickel/manganese the molar ratio, expressed as the free metal, is in the range 0.2/-2/1.

12. A process according to claim 1 wherein the operating conditions include a temperature in the approximate range 400°-900° F. and the amount of hydrogen expressed as the mole ratio hydrogen to reactant feed is in the approximate range 1:1 to 20:1 and the pressure is in the approximate range 50-600 psi.

* * * * *

UNITED STATES PATENT AND TRADEMARK OFFICE
CERTIFICATE OF CORRECTION

PATENT NO. : 4,304,943

DATED : December 8, 1981

INVENTOR(S) : Geir Bjornson

It is certified that error appears in the above-identified patent and that said Letters Patent are hereby corrected as shown below:

Column 12, line 66, delete "on" and insert therefor --- or ---.

Signed and Sealed this

Fourth Day of May 1982

[SEAL]

Attest:

GERALD J. MOSSINGHOFF

Attesting Officer     Commissioner of Patents and Trademarks